(12) United States Patent
Foley

(10) Patent No.: US 12,209,069 B2
(45) Date of Patent: Jan. 28, 2025

(54) FATTY ACID TERPENE ALCOHOL ESTERS

(71) Applicant: P2 Science, Inc., Woodbridge, CT (US)

(72) Inventor: Patrick Foley, New Haven, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 17/746,626

(22) Filed: May 17, 2022

(65) Prior Publication Data

US 2022/0380291 A1 Dec. 1, 2022

Related U.S. Application Data

(60) Provisional application No. 63/189,544, filed on May 17, 2021.

(51) Int. Cl.
*C07C 67/08* (2006.01)
(52) U.S. Cl.
CPC .................................. *C07C 67/08* (2013.01)
(58) Field of Classification Search
CPC ........ C07C 67/08; C07C 69/26; C07C 69/533
See application file for complete search history.

(56) References Cited

U.S. PATENT DOCUMENTS

| | | | |
|---|---|---|---|
| 2,020,298 A | 11/1935 | Carothers et al. | |
| 3,035,987 A * | 5/1962 | Weitzel | C07C 51/09 568/877 |
| 3,335,053 A | 8/1967 | Weitzel | |
| 3,829,505 A | 8/1974 | Herold et al. | |
| 3,980,697 A | 9/1976 | El-Chahawi et al. | |
| 4,021,507 A | 5/1977 | Ford | |
| 4,070,386 A | 1/1978 | Rossmy | |
| 4,218,379 A | 8/1980 | Harris et al. | |
| 4,366,270 A | 12/1982 | Rüter | |
| 4,381,416 A | 4/1983 | Kyo et al. | |
| 5,030,768 A | 7/1991 | Chen et al. | |
| 5,264,547 A | 11/1993 | Yamaguchi et al. | |
| 5,292,845 A | 3/1994 | Kawasaki | |
| 5,531,910 A | 7/1996 | Severns et al. | |
| 5,545,601 A | 8/1996 | Le-Khac | |
| 5,562,847 A | 10/1996 | Waite et al. | |
| 5,616,679 A | 4/1997 | Fies et al. | |
| 6,001,789 A | 12/1999 | Trinh et al. | |
| 6,117,521 A | 9/2000 | Yoshida et al. | |
| 6,348,618 B1 | 2/2002 | Anderson et al. | |
| 6,355,845 B1 | 3/2002 | Clement et al. | |
| 6,359,101 B1 | 3/2002 | O'Connor et al. | |
| 6,369,025 B1 | 4/2002 | Trinh et al. | |
| 7,355,066 B1 | 4/2008 | Johnson et al. | |
| 7,445,790 B2 | 11/2008 | Oguchi et al. | |
| 9,068,091 B2 | 6/2015 | Hofstra et al. | |
| 9,200,298 B2 | 12/2015 | Lee et al. | |
| 9,982,073 B2 | 5/2018 | Ghandi et al. | |
| 10,059,801 B2 | 8/2018 | Foley et al. | |
| 10,844,169 B2 | 11/2020 | Foley et al. | |
| 11,008,271 B2 | 5/2021 | Yang et al. | |
| 11,518,850 B2 | 12/2022 | Foley et al. | |
| 11,827,746 B2 | 11/2023 | Foley et al. | |
| 11,872,300 B2 | 1/2024 | Foley et al. | |
| 2004/0152830 A1 | 8/2004 | Kim et al. | |
| 2004/0202689 A1 | 10/2004 | Subramanyan et al. | |
| 2005/0256347 A1 | 11/2005 | Goebbel et al. | |
| 2006/0018977 A1 | 1/2006 | Bruza et al. | |
| 2008/0311066 A1 | 12/2008 | Samain et al. | |
| 2009/0169652 A1 * | 7/2009 | Osborne | A61K 8/9789 424/727 |
| 2012/0046244 A1 | 2/2012 | Rogers et al. | |
| 2013/0202543 A1 | 8/2013 | Küper et al. | |
| 2017/0057940 A1 | 3/2017 | Foley et al. | |
| 2017/0088536 A1 | 3/2017 | Foley et al. | |
| 2017/0283553 A1 | 10/2017 | Foley et al. | |
| 2018/0071188 A1 | 3/2018 | Barhoum et al. | |
| 2019/0184049 A1 | 6/2019 | Salaam-Zayid et al. | |
| 2020/0179247 A1 | 6/2020 | Verdier et al. | |
| 2020/0392287 A1 | 12/2020 | Foley et al. | |
| 2022/0259524 A1 * | 8/2022 | Struillou | C11D 3/38627 |

FOREIGN PATENT DOCUMENTS

| | | | |
|---|---|---|---|
| CN | 104307428 | | 1/2015 |
| DE | 10 2005 025 739 A1 | | 12/2006 |
| EP | 19182885.4 | * | 6/2019 |
| GB | 841903 | | 7/1960 |
| JP | 2006-273796 A | | 10/2006 |
| JP | 2008-050415 A | | 3/2008 |
| JP | 2019005262 A | | 1/2019 |
| JP | 6745563 | * | 8/2020 |
| JP | 2020152663 A | | 9/2020 |
| WO | WO 2006/057086 | | 6/2006 |
| WO | WO 2016/033437 A2 | | 3/2016 |
| WO | WO 2019/028053 A1 | | 2/2019 |

(Continued)

OTHER PUBLICATIONS

JP6745563 translated (Year: 2020).*
Dictionary (p. 1, obtained from internet 2024) (Year: 2024).*
Desaubry, et al., "Toward Higher Polyprenols Under 'Prebiotic' Conditions," *Tetrahedron Letters*, Issue 44, pp. 6959-6961, (2003); Doi: 10.1016/S0040-4039(03)01624-1.
Halbert, S., "Plant-derived compounds and extracts with potential as aphid repellents", *Ann Appl Biol.*, 154(2), pp. 303-307, (2009).
Hanson, "Chiral Acylic Synthetic Intermediates from Readily Available Monoterpenoids," *Journal of Chemical Research*, vol. 39, pp. 617-621, (2015).
Marchal et al., "Lyotropic liquid crystal behaviour of azelate and succinate monoester surfactants based on fragrance alcohols", *Journal of Colloid and Interface Science*, vol. 321, pp. 177-185, (2008).

(Continued)

*Primary Examiner* — Yevgeny Valenrod
*Assistant Examiner* — Blaine G Doletski
(74) *Attorney, Agent, or Firm* — Hoxie & Associates LLC

(57) ABSTRACT

The present disclosure is directed to novel derivatives of terpenes, particularly derivatives of terpene alcohols, and methods of making them, compositions comprising them, and methods for using them.

18 Claims, No Drawings

(56) References Cited

FOREIGN PATENT DOCUMENTS

| WO | WO 2019/029808 A1 | 2/2019 |
|---|---|---|
| WO | WO 2019/059375 | 3/2019 |

OTHER PUBLICATIONS

Nagai, "The Formation of Ethers from dl-Citronellol in the Presence of Boron Trifluoride Etherate," *Bulletin of the Chemical Society of Japan*, vol. 49, No. 1, pp. 265-269, (1976).

Nagai, et al., "The Formation of Ethers from Unsaturated Aliphatic Alcohols in the Presence of Boron Trifluoride Etherate," *Bulletin of the Chemical Society of Japan*, vol. 51, No. 11, pp. 3273-3276, (1978).

PubChem CID 13469549, 11 pages, (2007); retrieved on Sep. 10, 2018 from http://pubchem.ncbi.nlm.nih.gov/compound/013469549#section=Top>.

PubChem, OPEN Chemistry Database, PubChem CID 8892, pp. 4, (2004), 60 pages.

PubChem, OPEN Chemistry Database, PubChem SID 105168722, PubChem CID 112049, (2011), 7 pages.

PubChem, OPEN Chemistry Database, PubChem SID 355155508, PubChem CID 114416, (2018), 6 pages.

PubChem, OPEN Chemistry Database, PubChem CID 11172890, (2006), 10 pages.

PubChem, OPEN Chemistry Database, PubChem CID 23297377, (2007), 9 pages.

Takahashi, et al., "Cationic Polymerization Behavior of Alkoxyallenes," *Macromolecules*, vol. 28, No. 4, pp. 866-869, (1995).

Wheeler et al. "2,3-Dihydrofarnesyl and citronellyl esters in the paracloacal gland secretions of the brown caiman (*Caiman crocodilus fuscus*) from Costa Rica", Biochemical Systematics and Ecology, vol. 27, pp. 27-32, (1998).

Worzakowska, "Synthesis, Characterization, and Thermal Properties of New Flavor Compounds," *J Therm Anal Calorim*, vol. 116, pp. 727-736, (2014); DOI: 10.1007/s10973-013-3541-1.

Worzakowska, "Thermal Properties of Neryl Long-Chain Esters Obtained Under Microwave Irradiation," *J Therm Anal Calorim*, vol. 120, pp. 1715-1722, (2015); DOI: 10.1007/s10973.015-4489-0.

Barrere, et al., "Polyester synthesis in aqueous miniemulsion," *Polymer* (2003), 44(10), 2833-2841.

Paroul, et al., "Solvent-Free Production of Bioflavors by Enzymatic Esterification of Citronella (*Cymbopogon winterianus*) Essential Oil", Applied Biochemistry and Biotechnology, 166: 13-21 (2012).

Rashid, A., et al., "Enzymatic Synthesis of Citronellyl Palmitate in Organic Media: Process Optimization and Kinetic Evaluation", Asian Journal of Chemistry, 28(2):298-300 (2016).

Schlenk, W. Jr., "Asymmetric urea inclusion lattice. II. Configurational lattice coordination of the guest molecules," *Justus Liebigs Annalen der Chemie* (1973), (7), 1156-78.

Swift, K., "Catalytic Transformations of the Major Terpene Feedstocks", Topics in Catalysis, 27(1-4): 143-155 (2004).

\* cited by examiner

FATTY ACID TERPENE ALCOHOL ESTERS

CROSS-REFERENCE TO RELATED APPLICATIONS

This U.S. nonprovisional application claims priority to, and the benefit of, U.S. Provisional Application No. 63/189,544, filed on May 17, 2021, the contents of which are hereby incorporated by reference in its entirety.

FIELD OF INVENTION

The present disclosure is directed to novel derivatives of terpenes, particularly ester derivatives of terpene alcohols, and methods of making them, compositions comprising them, and methods for using them.

BACKGROUND

Terpenes and terpene derivatives constitute one of the most diverse, commercially sought after, and industrially important classes of natural products. Terpenes occur in all organisms and are particularly prevalent in plants, from which they are industrially isolated. The ready commercial access and low-cost of terpenes continually drives innovation into their chemical derivatization which find use in polymer science, the flavor & fragrance industry, the cosmetic industry, the pharmaceutical industry, and as surfactants, plastic additives, and other industrial uses.

While base terpenes are inexpensive and widely available ($C_{5n}H_{8n}$ derivatives, n=1, 2, 3, etc.), chemically functionalized terpenes (terpenoids) are more useful, especially terpene alcohols. Common monoterpene alcohols include the following:

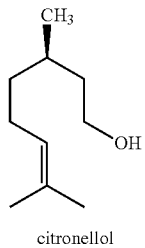
citronellol

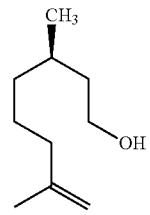
isocitronellol

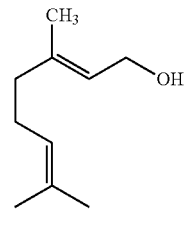
geraniol

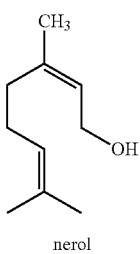
nerol

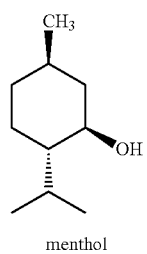
menthol

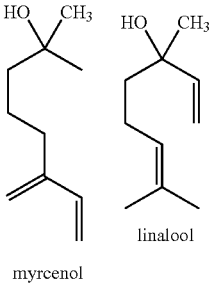
myrcenol / linalool

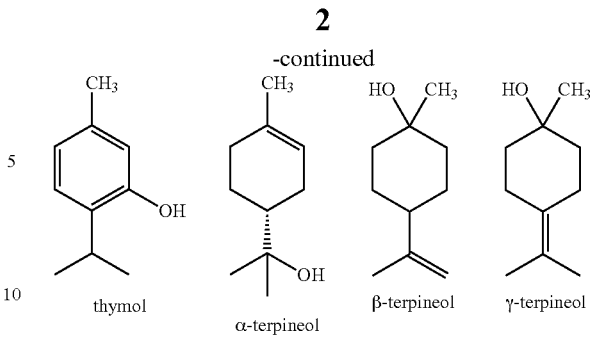

thymol    α-terpineol    β-terpineol    γ-terpineol

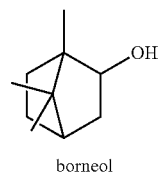
borneol

In addition to monoterpene alcohols, there are also inexpensive and widely available sesquiterpene alcohols, such as:

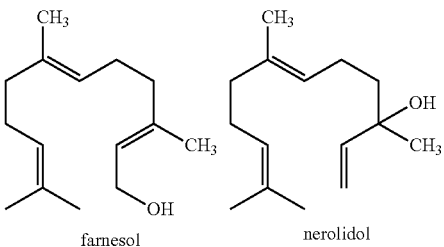
farnesol      nerolidol

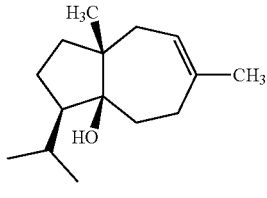
carotol

Terpene alcohol derivatives also include polymers and oligomers of terpene alcohols. For example, citronellol has been formed into useful oligomeric and polymeric products having the following structure:

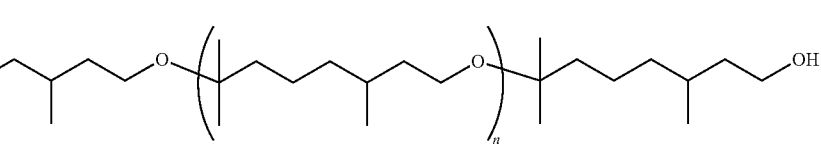

wherein n: 0-20 (e.g., 0-3). Dimers, trimers, and other oligomers of citronellol have been described. See, e.g., US2017/0283553, US2020/0165383, and US2020/0392287, the contents of each of which are hereby incorporated by reference in their entireties.

Fatty acid esters are a multimillion dollar annual industry. While natural fats and oils are esters of fatty acids with glycerol, most industrially useful fatty acid esters are esters of fatty acids with monohydroxy alcohols, especially hydrophobic monohydroxy alcohols, such as fatty alcohols. These compounds find a variety of uses, for example, as emollients, lubricants, defoamers, adjuvants and others. These compounds are commonly found in personal care and cosmetic compositions.

There remains a need for new compounds in this field, with new or different properties, such as improved stability, improved biodegradability, or improved environmental impact. It would be especially advantageous to have new fatty acid esters sourced from renewable resources.

BRIEF SUMMARY OF THE INVENTION

The present disclosure provides fatty acid terpene alcohol esters, derived from terpene alcohols, and oligomers and derivatives thereof, and fatty acids, such as lauric acid, palmitic acid, myristic acid, and derivatives thereof. These compounds are useful in numerous types of compositions, and numerous roles. For example, these compounds may be used as emollients, lubricants, defoamers, adjuvants and other uses, and are especially useful as ingredients in personal care compositions and cosmetic compositions.

In a second aspect, the present disclosure provides a method of preparing such compounds.

In a third aspect, the present disclosure provides compositions and products comprising such compounds. In some embodiments, said compounds are useful in a variety of applications, including as or in cosmetics, soaps, hair care products, fragrances, sunscreens, plastic additives, paints, coatings, lubricants, and surfactants.

DETAILED DESCRIPTION OF THE INVENTION

As used herein, the term "terpene alcohol" refers to a naturally terpene or terpenoid having or modified to have at least one alcohol functionality. The term includes both naturally occurring terpene alcohols, and alcohols derived from naturally occurring terpenes, such as by double bond oxidation, ketone reduction, or the like. As used herein, the term "terpene derivative" or "terpene alcohol derivatives" includes saturated and partially saturated derivatives of terpenes and terpene alcohols. Terpenes, terpene alcohols and other terpenoids commonly have 1, 2, 3 or more double bonds. In a saturated derivative all double bonds are hydrogenated, while in a partially saturated derivative, at least one double bond is hydrogenated, but at least one double bond is not. In this context, the double bonds of an aromatic ring are included; thus, a benzene ring can be considered to be partially saturated to form a cyclohexadiene or a cyclohexene ring, or fully saturated to form a cyclohexane ring.

In a first aspect, the present disclosure provides a fatty acid terpene alcohol ester compound (Compound 1) of the general formula (I):

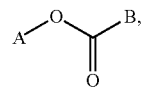

Formula (I)

in free or salt form, wherein A is the core of a terpene alcohol or derivative thereof, and wherein B is the saturated or unsaturated hydrocarbon chain, or derivative thereof, of a natural or unnatural fatty acid. It is further understood that "derivative thereof" includes, but is not limited to, hydrogenation derivatives thereof, including partially hydrogenated and fully hydrogenated derivatives of unsaturated fatty acids. In a preferred embodiment, the product compound of Formula I is an isodecyl ester (i.e., group A is an isodecyl group).

It is understood that in the phrase "A is the core of a terpene alcohol or derivative thereof, that the terpene alcohol, or derivative thereof, from which the compound of Formula I is derived has the formula A-OH. Thus, the ester functional group of the compound of Formula I is formed, or is formable by, the condensation reaction as follows:

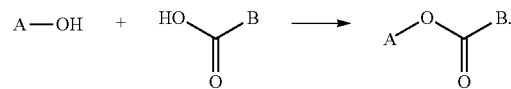

It is similarly understood that in the phrase "B is the saturated or unsaturated hydrocarbon chain, or derivative thereof, of a natural or unnatural fatty acid" that HOOC—B is a natural or unnatural fatty acid referred to, as shown above.

In further embodiments of the first aspect, the present disclosure provides as follows:

1.1 Compound 1, wherein A is the core of a terpene alcohol, or derivative thereof, wherein said terpene is a monoterpene, sesquiterpene, diterpene, sesterterpene, or triterpene.

1.2 Compound 1, wherein A is the core of a terpene alcohol, or derivative thereof, wherein said terpene is a monoterpene or sesquiterpene.

1.3 Compound 1, wherein A is the core of a terpene alcohol, or derivative thereof, wherein said terpene is a monoterpene (e.g., A is an isodecyl moiety).

1.4 Compound 1, wherein A is the core of a terpene alcohol, or derivative thereof, wherein said terpene alcohol is selected from citronellol, isocitronellol, geraniol, nerol, menthol, myrcenol, linalool, thymol, α-terpineol, β-terpineol, γ-terpineol, borneol, farnesol, nerolidol, and carotol.

1.5 Compound 1.4, wherein said terpene alcohol is selected from citronellol, geraniol, nerol, myrcenol, linalool, and farnesol.

1.6 Compound 1.5, wherein said terpene alcohol is selected from citronellol, myrcenol, linalool, and farnesol.

1.7 Compound 1, wherein A is the core of a terpene alcohol, or derivative thereof, wherein said terpene alcohol, or derivative, is an oligomer of citronellol.

1.8 Compound 1 or any of 1.1-1.7, wherein said terpene alcohol, or derivative thereof, has its natural unsaturation.

1.9 Compound 1 or any of 1.1-1.7, wherein said terpene alcohol, or derivative thereof, is partially unsaturated (e.g., monounsaturated or diunsaturated).

1.10 Compound 1 or any of 1.1-1.7, wherein said terpene alcohol, or derivative thereof, is fully saturated (e.g., said terpene alcohol is a fully saturated monoterpene derivative, e.g., an isodecyl moiety).

1.11 Compound 1, wherein A is selected from the group consisting of:

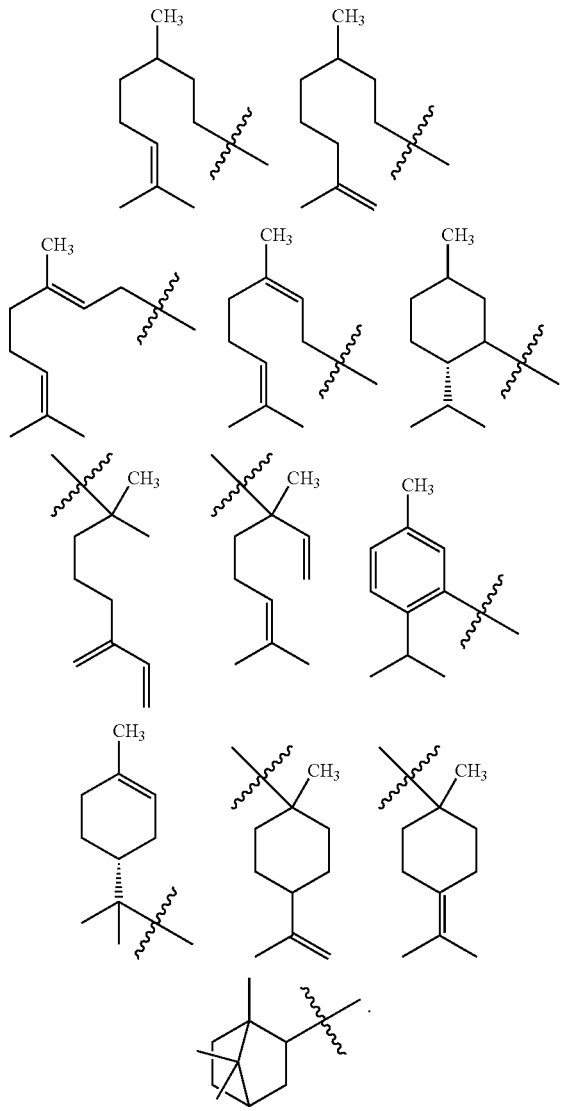

1.12 Compound 1, wherein A is selected from the group consisting of:

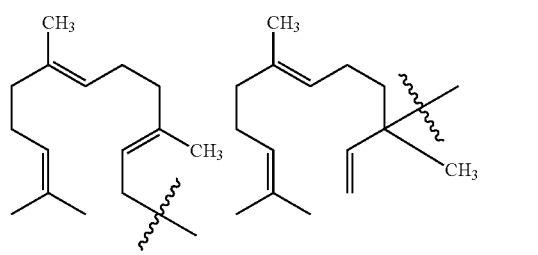

1.13 Compound 1, wherein A is selected from the group consisting of:

1.14 Compound 1, wherein A is selected from the group consisting of:

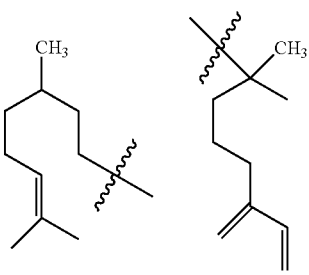

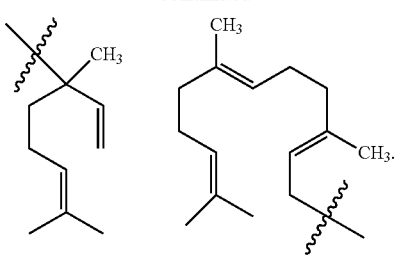 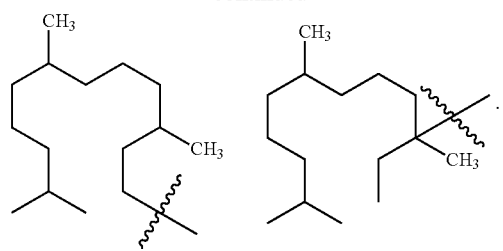
1.15 Compound 1, wherein A is:
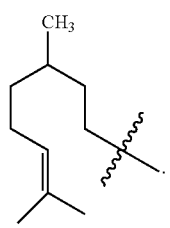 [SMILES: *CCC(C)CCC=C(C)C]
1.17 Compound 1, wherein A is selected from the group consisting of:
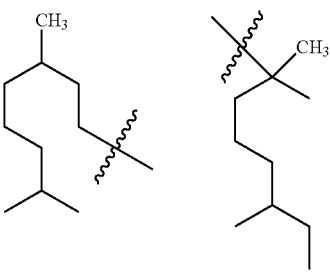
1.16 Compound 1, wherein A is selected from the group consisting of:
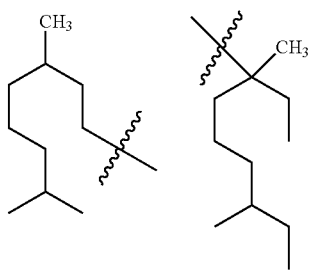
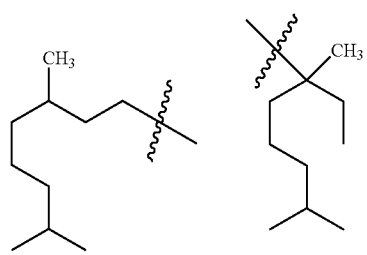 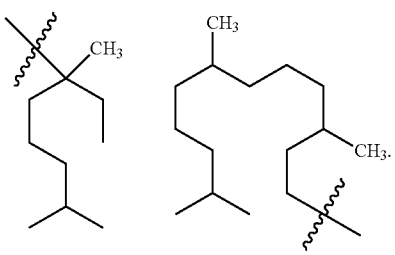
1.18 Compound 1, wherein A is:
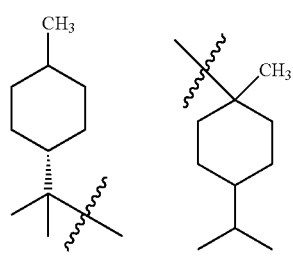 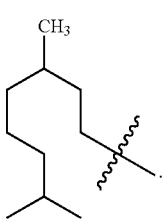 [SMILES: *CCC(C)CCCC(C)C]

1.19 Compound 1, wherein A is:

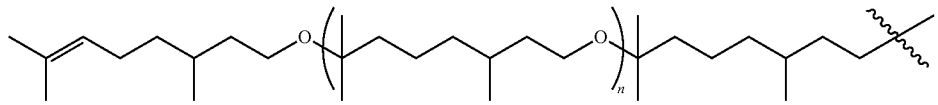

wherein n is an integer from 0-20 (e.g., 0-3, 0, 1 or 2).

1.20 Compound 1, wherein A is:

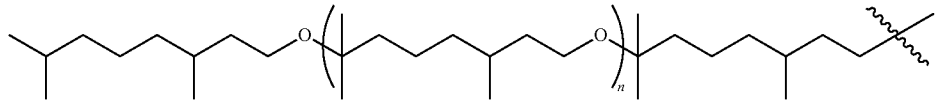

wherein n is an integer from 0-20 (e.g., 0-3, 0, 1 or 2).

1.21 Compound 1, or any of 1.1-1.20, wherein B is the saturated or unsaturated hydrocarbon chain, or derivative thereof, of a C4 to C28 fatty acid (i.e., group B has a C3 to C27 hydrocarbon chain).

1.22 Compound 1, or any of 1.1-1.20, wherein B is the saturated or unsaturated hydrocarbon chain, or derivative thereof, of a C6 to C12 fatty acid (i.e., group B has a C5 to C11 hydrocarbon chain).

1.23 Compound 1, or any of 1.1-1.20, wherein B is the saturated or unsaturated hydrocarbon chain, or derivative thereof, of a C13 to C21 fatty acid (i.e., group B has a C12 to C20 hydrocarbon chain).

1.24 Compound 1, or any of 1.1-1.20, wherein B is the saturated or unsaturated hydrocarbon chain, or derivative thereof, of a C22 to C28 fatty acid (i.e., group B has a C21 to C27 hydrocarbon chain).

1.25 Compound 1, or any of 1.1-1.20, wherein B is the saturated or unsaturated hydrocarbon chain, or derivative thereof, of a C8, C9, C10, C12, C14, C16, or C18 fatty acid (i.e., group B has a C7, C8, C9, C11, C13, C15, or C17 hydrocarbon chain).

1.26 Compound 1, any one of 1.1-1.25, wherein B is an unsaturated hydrocarbon chain, e.g., monounsaturated, diunsaturated or triunsaturated.

1.27 Compound 1.26, wherein B is $-(CH_2)_xCH=CH(CH_2)_yCH_3$, wherein x is an integer from 3 to 18 (e.g., 2, 3, 4, 7 or 9), and y is an integer from 1 to 8 (e.g., 1, 2, 3, 4, 5, 7, or 8).

1.28 Compound 1.26, wherein B is $-(CH_2)_xCH=CH(CH_2)_aCH=CH(CH_2)_yCH_3$, wherein x is an integer from 3 to 18 (e.g., 2, 3, 4, 7, 9 or 11), a is an integer from 1 to 5 (e.g., 1 or 3), and y is an integer from 1 to 8 (e.g., 1, 2, 3, 4, 5, 7, or 8).

1.29 Compound 1.26, wherein B is $-(CH_2)_xCH=CH(CH_2)_aCH=CH(CH_2)_bCH=CH(CH_2)_yCH_3$, wherein x is an integer from 3 to 18 (e.g., 2, 3, 4, 7, 9 or 11), a and b are each independently an integer from 1 to 5 (e.g., 1, 3 or 5), and y is an integer from 1 to 8 (e.g., 1, 2, 3, 4, 5, 7, or 8).

1.30 Any one of compounds 1.1-1.29, wherein each double bond (—CH=CH—) has the cis orientation.

1.31 Any one of compounds 1.1-1.29, wherein each double bond (—CH=CH—) has the trans orientation.

1.32 Any one of compounds 1.1-1.29, wherein at least one double bond (—CH=CH—) has the cis orientation and one double bond has the trans orientation.

1.33 Compound 1, any one of 1.1-1.25, wherein B is a saturated hydrocarbon chain, e.g., B is $-(CH_2)_xCH_3$, wherein x is an integer from 3 to 26 (e.g., 3, 4, 5, 6, 7, 8, 9, 10, 11, 12, 13, 14, 15, 16, 17, 18, 19, 20, 21, 22, 23, 24, 25, or 26).

1.34 Compound 1, or any of 1.1-1.33, wherein the compound is selected from the group consisting of:

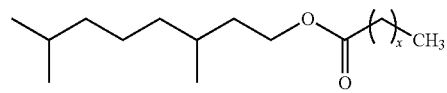

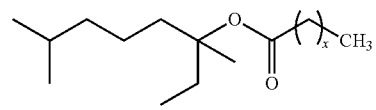

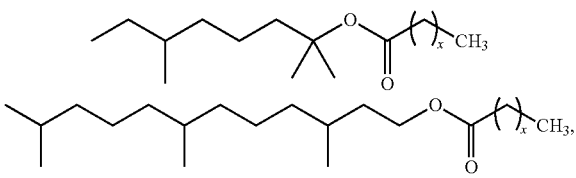

wherein x is an integer selected from 7, 8, 9, 11, 13, 15 and 17.

1.35 Compound 1.34, wherein x is an integer selected from 8, 9, and 11.

1.36 Compound 1.34, wherein x is 8.

1.37 Compound 1.34, wherein x is 9.

1.38 Compound 1.34, wherein x is 11.

1.39 Compound 1.34, wherein x is 17.

1.40 Compound 1, or any of 1.1-1.39, wherein group A is an isodecyl group, e.g., selected from 2,4-dimethyloctan-2-yl, 2,6-dimethyl-octan-1-yl, 2,6-dimethyloctan-2-yl, 3,7-dimethyloctan-1-yl, and 3,7-dimethyloctan-3-yl.

1.41 Compound 1, or any of 1.1-1.40, wherein group B is $CH_3(CH_2)_{14}-$, $CH_3(CH_2)_{10}-$, or cis-$CH_3(CH_2)_7CH=CH(CH_2)_7-$.

1.42 Compound 1, or any of 1.1-1.41, wherein the compound is selected from the group consisting of:

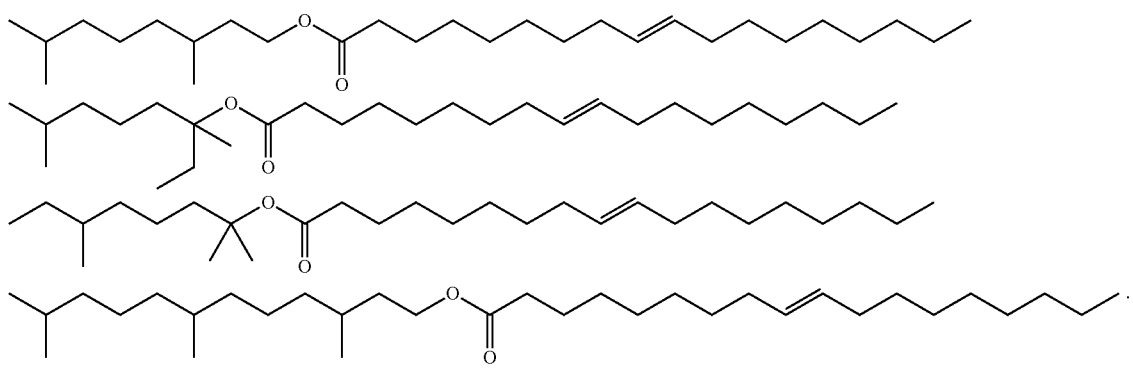
1.43 Compound 1, or any of 1.1-1.41, wherein the compound is selected from the group consisting of:
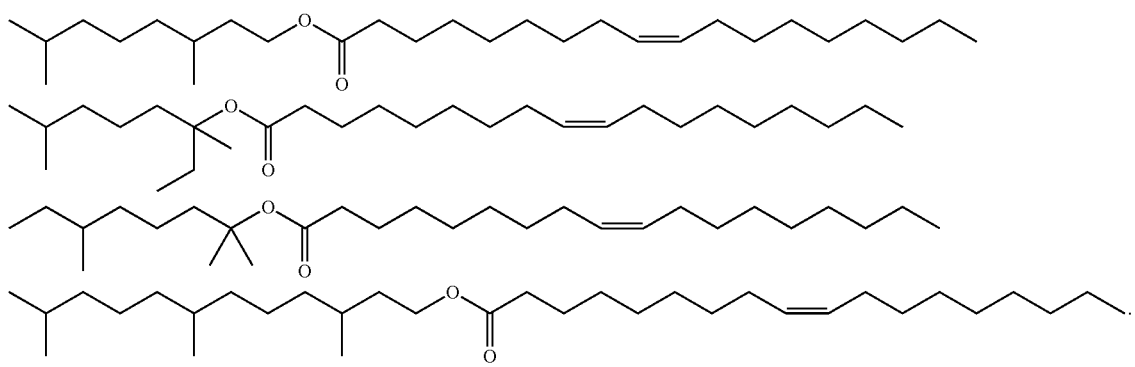
1.44 Compound 1, or any of 1.1-1.41, wherein the compound is selected from the group consisting of:
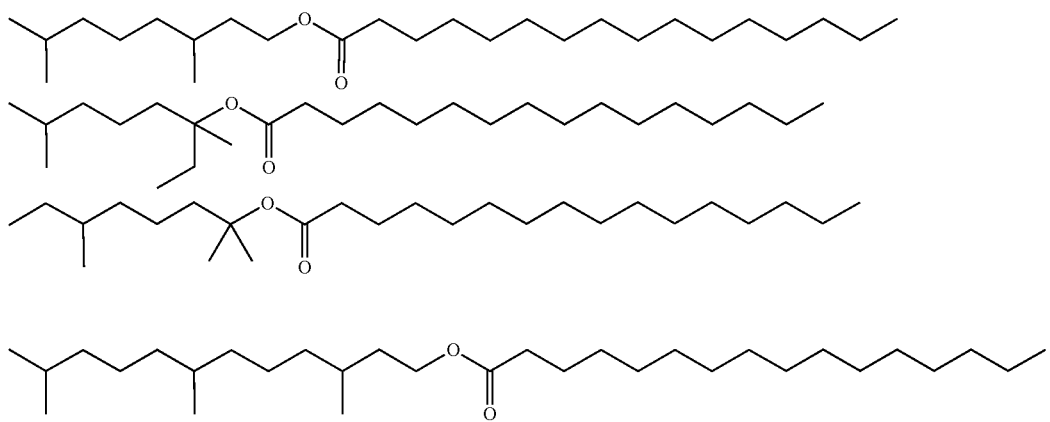
1.45 Compound 1, or any of 1.1-1.41, wherein the compound is selected from the group consisting of:
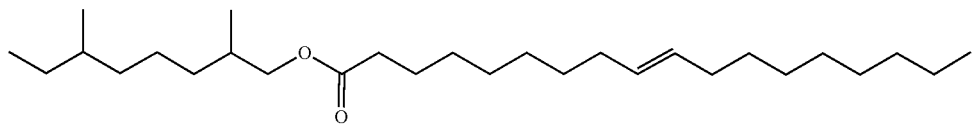

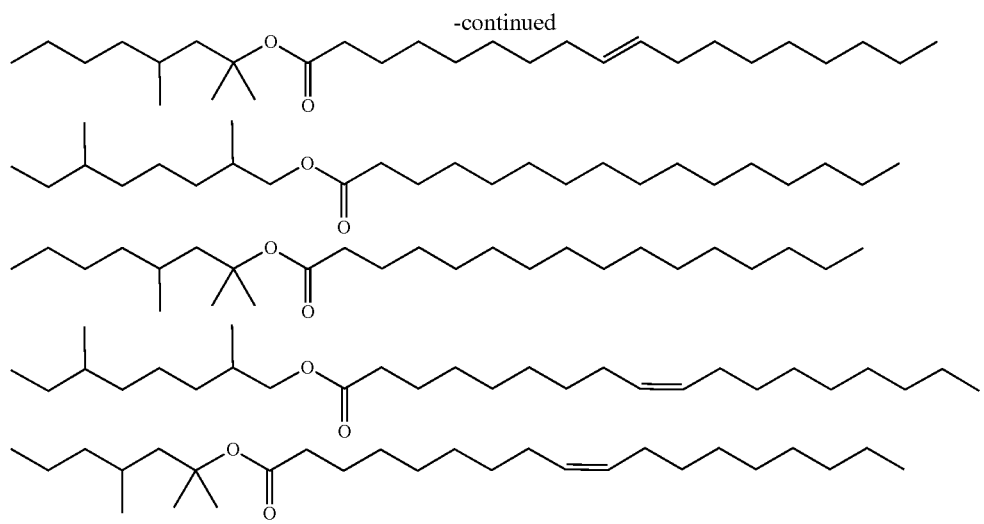

-continued 1.46 Any compounds 1.1-1.45, wherein the compound has a single stereogenic center within the substituent A and that center has the R configuration.
1.47 Any compounds 1.1-1.45, wherein the compound has a single stereogenic center within the substituent A and that center has the S configuration.
1.48 Any compounds 1.1-1.45, wherein the compound has two or three stereogenic centers within the substituent A and they each have the R configuration.
1.49 Any compounds 1.1-1.45, wherein the compound has two or three stereogenic centers within the substituent A and they each have the S configuration.
1.50 Compound 1, or any of 1.1-1.49, wherein the compound has a refractive index from 1.35 to 1.55, e.g., 1.40 to 1.50, or 1.42 to 1.48, or 1.43 to 1.46, or 1.44-1.45.
1.51 Compound 1, or any of 1.1-1.50, wherein the compound has a surface tension of 15 to 35 mN/m, e.g., 20 to 30 mN/m, or 22 to 28 mN/m, or 23 to 27 mN/m, or 24 to 26 mN/m, or about 25 mN/m.

The term "isodecyl" as used herein refers to any 10-carbon saturated alkyl chain that is not linear (i.e., not n-decyl).

The compounds provided by the present disclosure offer numerous improved benefits over existing compounds used for the same purpose. For example, Compound 1 et seq. provides one or more of: (a) lower melting point, (b) better lubricity, (c) better spreading (e.g., better spontaneous spreading on the skin), (d) higher refractive index, (e) better hydrolytic stability, and (f) better enzymatic stability. Without being bound by theory, it is believed that compounds as disclosed herein having an isodecyl group are provide particularly beneficial improvements over compounds of the prior art, for example, due to the increased extent of branching in the alkyl chain. Surface tension is one of the physical factors which helps provide the compounds with improved emolliency, lubricity, spreadability and "play" (i.e., feel on the skin and hair) compared to known compounds used for similar purposes. Preferably, compounds of the present disclosure have a surface tension between 15 and 35 milliNewtons/meter (mN/m). Refractive index is important from an appearance standpoint, as a higher refractive index provides for a shinier or glossier product. Preferably, compounds of the present disclosure have a refractive index between 1.35 and 1.55.

The term "alkyl" as used herein refers to a monovalent or bivalent, branched or unbranched saturated hydrocarbon group having from 1 to 20 carbon atoms, typically although, not necessarily, containing 1 to about 12 carbon atoms, such as methyl, ethyl, n-propyl, isopropyl, n-butyl, isobutyl, t-butyl, octyl, and the like. The term alkyl also may include cycloalkyl groups. Thus, for example, the term C6 alkyl would embrace cyclohexyl groups, the term C5 would embrace cyclopentyl groups, the term C4 would embrace cyclobutyl groups, and the term C3 would embrace cyclopropyl groups. In addition, as the alkyl group may be branched or unbranched, any alkyl group of n carbon atoms would embrace a cycloalkyl group of less than n carbons substituted by additional alkyl substituents. Thus, for example, the term C6 alkyl would also embrace methylcyclopentyl groups, or dimethylcyclobutyl or ethylcyclobutyl groups, or trimethylcyclopropyl, ethylmethylcyclopropyl or propylcyclopropyl groups.

The term "alkenyl" as used herein refers to a monovalent or bivalent, branched or unbranched, unsaturated hydrocarbon group typically although not necessarily containing 2 to about 12 carbon atoms and 1-10 carbon-carbon double bonds, such as ethylene, n-propylene, isopropylene, n-butylene, isobutylene, t-butylene, octylene, and the like. In like manner as for the term "alkyl", the term "alkenyl" also embraces cycloalkenyl groups, both branched an unbranched with the double bond optionally intracyclic or exocyclic.

The term "alkynyl" as used herein refers to a monovalent or bivalent, branched or unbranched, unsaturated hydrocarbon group typically although not necessarily containing 2 to about 12 carbon atoms and 1-8 carbon-carbon triple bonds, such as ethyne, propyne, butyne, pentyne, hexyne, heptyne, octyne, and the like. In like manner as for the term "alkyl", the term "alkynyl" also embraces cycloalkynyl groups, both branched an unbranched, with the triple bond optionally intracyclic or exocyclic.

The term "aryl" as used herein refers to an aromatic hydrocarbon moiety comprising at least one aromatic ring of 5-6 carbon atoms, including, for example, an aromatic hydrocarbon having two fused rings and 10 carbon atoms (i.e., a naphthalene).

By "substituted" as in "substituted alkyl," "substituted alkenyl," "substituted alkynyl," and the like, it is meant that in the alkyl, alkenyl, alkynyl, or other moiety, at least one hydrogen atom bound to a carbon atom is replaced with one or more non-hydrogen substituents, e.g., by a functional group.

The terms "branched" and "linear" (or "unbranched") when used in reference to, for example, an alkyl moiety of $C_a$ to $C_b$ carbon atoms, applies to those carbon atoms defining the alkyl moiety. For example, for a $C_4$ alkyl moiety, a branched embodiment thereof would include an isobutyl, whereas an unbranched embodiment thereof would be an n-butyl. However, an isobutyl would also qualify as a linear $C_3$ alkyl moiety (a propyl) itself substituted by a $C_1$ alkyl (a methyl).

Unless otherwise specified, any carbon atom with an open valence may be substituted by an additional functional group. Examples of functional groups include, without limitation: halo, hydroxyl, sulfhydryl, $C_1$-$C_{20}$ alkoxy, $C_2$-$C_{20}$ alkenyloxy, $C_2$-$C_{20}$ alkynyloxy, $C_5$-$C_{20}$ aryloxy, acyl (including $C_2$-$C_{20}$ alkylcarbonyl (—CO-alkyl) and $C_6$-$C_{20}$ arylcarbonyl (—CO-aryl)), acyloxy (—O-acyl), $C_2$-$C_{20}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{20}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-substituted $C_1$-$C_{20}$ alkylcarbamoyl (—(CO)—NH($C_1$-C20 alkyl)), di-substituted alkylcarbamoyl (—(CO)—N($C_1$-C20 alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{20}$ alkyl)-substituted amino, mono- and di-($C_5$-$C_{20}$ aryl)-substituted amino, $C_2$-$C_{20}$ alkylamido (—NH—(CO)-alkyl), $C_5$-$C_{20}$ arylamido (—NH—(CO)-aryl), imino (—CR=NH where R=hydrogen, $C_1$-C20 alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{20}$ alkylsulfanyl (—S-alkyl; also termed "alkylthio"), arylsulfanyl (—S-aryl; also termed "arylthio"), $C_1$-$C_{20}$ alkylsulfinyl (—(SO)-alkyl), $C_5$-$C_{20}$ arylsulfinyl (—(SO)-aryl), $C_1$-$C_{20}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—P$_2$),-phosphino (—PH$_2$), mono- and di-($C_1$-$C_{20}$ alkyl)-substituted phosphino, mono- and di-($C_5$-$C_{20}$ aryl)-substituted phosphino; and the hydrocarbyl moieties such as $C_1$-$C_{20}$ alkyl (including $C_1$-$C_{18}$ alkyl, further including $C_1$-$C_{12}$ alkyl, and further including $C_1$-$C_6$ alkyl), $C_2$-$C_{20}$ alkenyl (including $C_2$-$C_{18}$ alkenyl, further including $C_2$-$C_{12}$ alkenyl, and further including $C_2$-$C_6$ alkenyl), $C_2$-$C_{20}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{20}$ aryl), and $C_6$-$C_{20}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. For example, the alkyl or alkenyl group may be branched. For example, the "substituent" is an alkyl group, e.g., a methyl group.

In a second aspect, the present disclosure provides a method of making the Compound 1, et seq., comprising the step of reacting a compound of the Formula A, or a salt thereof, with a compound of Formula B, or an ester, activated ester or acyl halide thereof, in a condensation reaction to form the compound of Formula I:

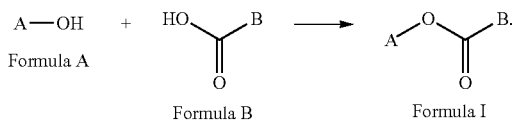

wherein substituents A and B, are as defined hereinabove. In some embodiments, the reaction is conducted by reacting the compound of Formula A and the compound of Formula B in the presence of an acid catalyst, optionally under dehydrating conditions. Preferably, the acid catalyst is selected from sulfuric acid, hydrochloric acid, phosphoric acid, toluenesulfonic acid, methanesulfonic acid, or an acidic ion exchange resin, such as an Amberlyst-type resin. In some embodiments, the reaction further comprises a dehydrating agent, such as sodium sulfate, magnesium sulfate, phosphorus pentoxide, or the like. In a preferred embodiment, the reaction comprises a mixture of sulfuric acid and magnesium sulfate, optionally in a hydrocarbon solvent, such as heptane. In some embodiments, the magnesium sulfate is first suspended in a hydrocarbon solvent, such as heptane, and concentration sulfuric acid is added to form, after removal of the solvent, a solid $MgSO_4/H_2SO_4$ adduct which can be used directly as an acidic catalyst for the condensation reaction. Preferably, this solid adduct is added directly to the neat reaction components (e.g., where the terpene alcohol of Formula A and/or the acid of Formula B is a liquid). In some embodiments, the reaction is conducted by reacting the compound of Formula A and the compound of Formula B in the presence of a coupling reagent, for example, 1,1-carbonyl-di-imidazole. In some embodiments, the reaction is conducted by reacting the compound of Formula A with an activated derivative of the compound of Formula B, such as an acyl halide or acid anhydride of the compound of Formula B. In some embodiments, the reaction is conducted under basic conditions, e.g., by reacting a compound of Formula A with a compound of Formula B, or an ester, activated ester, or acyl halide thereof, in the presence of a base (e.g., a hydroxide base, an alkoxide base, a carbonate base, a bicarbonate base, a hydride base, an organometallic base, or an amide base). In some embodiments, the reaction is conducted by reacting a salt compound of Formula A, such as a lithium salt, a sodium salt, or a potassium salt, with a compound of Formula B, or an ester, activated ester, or acyl halide thereof. In some embodiments said salt is formed in-situ. Suitable bases include sodium hydroxide, sodium methoxide, sodium ethoxide, sodium propoxide, sodium isopropoxide, sodium butoxide, sodium tert-butoxide, sodium carbonate, sodium bicarbonate, sodium hydride, sodium amide, potassium hydroxide, potassium methoxide, potassium ethoxide, potassium propoxide, potassium isopropoxide, potassium tert-butoxide, potassium carbonate, potassium bicarbonate, potassium hydride, potassium amide, lithium hydroxide, lithium methoxide, lithium tert-butoxide, lithium carbonate, lithium amide, lithium diisopropylamide, lithium hexamethyldisilazide, lithium tetramethylpiperidide, n-butyllithium, s-butyllithium, and t-butyllithium.

Suitable solvents and reactions conditions (concentration, time, temperature) for the conducting the reactions are generally known to those skilled in the art and are not limited in any way in the present disclosure. Depending on the choice of reagents, suitable solvents may include one or more of apolar, polar protic and/or polar aprotic solvents, for example hydrocarbons, ethers, and esters.

In some embodiments, the reaction is carried out at a temperature of −25° C. to 200° C. In a preferred embodiment, the reaction is run at 25 to 150° C., or 50 to 100° C. In some embodiments, the reaction is carried out for 0.1 to 100 hours. In a preferred embodiment the reaction is run for 0.5-12 hours, or 0.5 to 6 hours, or 1 to 3 hours.

The compound Formula A, used to make the Compound 1 et seq. of the present disclosure, is a terpene alcohol or a derivative thereof (e.g., a hydrogenated terpene alcohol). Preferably the terpene alcohol is obtained from or isolated from a natural renewable resource. For example, the each of the following terpene alcohols can be obtained by extraction from numerous plant species: citronellol, isocitronellol, geraniol, nerol, menthol, myrcenol, linalool, thymol, α-terpineol, β-terpineol, γ-terpineol, borneol, farnesol, nerolidol, and carotol. The essential oils of many trees and plants, such as rose oil, palmarosa oil, citronella oil, lavender oil, coriander oil, thyme oil, peppermint oil, and pine oil, have significant amounts of these terpene alcohols.

In a preferred embodiment, however, the terpene alcohols may be derived semi-synthetically (e.g., by double bond hydration reactions) from naturally derived terpenes. Terpenes are much more abundant in nature than the corresponding terpene alcohols. Common terpenes include: alpha-pinene, beta-pinene, alpha-terpinene, beta-terpinene, gamma-terpinene, delta-terpinene (terpinolene), myrcene, limonene, camphene, carene, sabinene, alpha-ocimene, beta-ocimene, alpha-thujene, and beta-thujene. Alpha-pinene is the most abundant naturally occurring terpene in nature, being present in a high concentration in various tree resins and oils, such as pine oil and oleoresin (and its derivative turpentine). Numerous terpene oils can be derived from the terpenes present in turpentine, pine oil, and similar materials. Turpentine is a major by-product of the paper and pulp industries, so using this material as a source for terpene alcohols would be both economical and environmentally friendly.

In addition, the terpene alcohols can be prepared semi-synthetically from either isobutylene, isoprenol, or ethanol. Ethanol, as well as methanol and tert-butanol, can be derived in large volumes from the fermentation of biorenewable sugars, such as from corn, cane sugar or beet sugar. Isobutylene can be derived from tert-butanol by elimination or from ethanol by mixed oxidation to acetaldehyde and acetone and aldol condensation, and isoprenol can be derived from isobutylene by reaction with formaldehyde, and formaldehyde can be made by oxidation of methanol. Methanol and ethanol can also be derived from the by-product fractions from commercial ethanol distillation (e.g., in the making of spirits). By these routes, the Compounds of the present disclosure can all be made entirely from biorenewable resources such as trees and plants.

Thus, in some embodiments of the present disclosure, the Method of making Compound 1 et seq. may further comprise one or more of the following steps: (1) harvesting of one or more crops or grains (e.g., corn, beets, sugarcane, barley, wheat, rye, or sorghum), (2) fermenting such harvested crops or grains, (3) obtaining from such fermentation one or more $C_{1-4}$ aliphatic alcohols (e.g., methanol, ethanol, isobutanol, tert-butanol, or any combination thereof), (4) converting said alcohols to isobutylene and/or isoprenol, (5) converting said isobutylene or isoprenol to one or more terpenes (e.g., alpha-pinene, beta-pinene, alpha-terpinene, beta-terpinene, gamma-terpinene, delta-terpinene (terpinolene), myrcene, limonene, camphene, carene, sabinene, alpha-ocimene, beta-ocimene, alpha-thujene, and beta-thujene); (6) extracting or isolating one or more terpenes from naturally occurring plant and tree extracts, such as essential oils and resins (e.g., rosin, dammars, mastic, sandarac, frankincense, elemi, turpentine, copaiba, oleoresin, pine oil, cannabis oil, coriander oil), and (7) converting such terpenes to one or more terpene alcohols (e.g., citronellol, isocitronellol, geraniol, nerol, menthol, myrcenol, linalool, thymol, α-terpineol, β-terpineol, γ-terpineol, borneol, farnesol, nerolidol, and carotol).

In another aspect, the present disclosure provides a composition comprising Compound 1 or any of 1.1 to 1.51, optionally in admixture with one or more pharmaceutically acceptable, cosmetically acceptable, or industrially acceptable excipients or carriers, for example, solvents, oils, surfactants, emollients, diluents, glidants, abrasives, humectants, polymers, plasticizer, catalyst, antioxidant, coloring agent, flavoring agent, fragrance agent, antiperspirant agent, antibacterial agent, antifungal agent, hydrocarbon, stabilizer, or viscosity controlling agent. In some embodiments, the composition is a pharmaceutical composition, or a cosmetic composition, or a sunscreen composition, or a plastic composition, or a lubricant composition, or a personal care composition (e.g., a soap, skin cream or lotion, balm, shampoo, body wash, hydrating cream, deodorant, antiperspirant, after-shave lotion, cologne, perfume, or other hair care or skin care product), or a cleaning composition (e.g., a surface cleaner, a metal cleaner, a wood cleaner, a glass cleaner, a body cleaner such as a soap, a dish-washing detergent, or a laundry detergent), or an air freshener.

In preferred embodiments, such Compositions comprise a Compound according to the present disclosure having an isodecyl group. In a particularly preferred embodiment, such Compositions also comprise another excipient having a decyl or isodecyl group, such as, decyl or isodecyl alcohol, decanoic or isodecanoic acids, decyl or isodecyl ethers, or decyl or isodecyl esters. For example, such Compositions may comprise a combination of one or more of the isodecyl compounds of Examples 1 to 11.

The compounds of the present disclosure, e.g., Compound 1, et seq., may be used with, e.g.: perfumes, soaps, insect repellants and insecticides, detergents, household cleaning agents, air fresheners, room sprays, pomanders, candles, cosmetics, toilet waters, pre- and aftershave lotions, talcum powders, hair-care products, body deodorants, anti-perspirants, shampoo, cologne, shower gel, hair spray, and pet litter.

Fragrance and ingredients and mixtures of fragrance ingredients that may be used in combination with the disclosed compound for the manufacture of fragrance compositions include, but are not limited to, natural products including extracts, animal products and essential oils, absolutes, resinoids, resins, and concretes, and synthetic fragrance materials which include, but are not limited to, alcohols, aldehydes, ketones, ethers, acids, esters, acetals, phenols, ethers, lactones, furansketals, nitriles, acids, and hydrocarbons, including both saturated and unsaturated compounds and aliphatic carbocyclic and heterocyclic compounds, and animal products.

In some embodiments, the present disclosure provides personal care compositions including, but not limited to, soaps (liquid or solid), body washes, skin and hair cleansers, skin creams and lotions (e.g., facial creams and lotions, face oils, eye cream, other anti-wrinkle products), ointments, sunscreens, moisturizers, hair shampoos and/or conditioners, deodorants, antiperspirants, other conditioning products for the hair, skin, and nails (e.g., shampoos, conditioners, hair sprays, hair styling gel, hair mousse), decorative cosmetics (e.g., nail polish, eye liner, mascara, lipstick, foundation, concealer, blush, bronzer, eye shadow, lip liner, lip balm,) and dermocosmetics.

In some embodiments, the personal care compositions may include organically-sourced ingredients, vegan ingredients, gluten-free ingredients, environmentally-friendly ingredients, natural ingredients (e.g. soy oil, beeswax, rosemary oil, vitamin E, coconut oil, herbal oils etc.), comedogenic ingredients, natural occlusive plant based ingredients (e.g. cocoa, shea, mango butter), non-comedogenic ingredients, bakuchiol (a plant derived compound used as a less-irritating, natural alternative to retinol), color active ingredients (e.g., pigments and dyes); therapeutically-active ingredients (e.g., vitamins, alpha hydroxy acids, corticosteroids, amino acids, collagen, retinoids, antimicrobial compounds), sunscreen ingredients and/or UV absorbing compounds, reflective compounds, oils (such as castor oil and olive oil, or high-viscosity oils), film formers, high molecular weight esters, antiperspirant active ingredients, glycol solutions, water, alcohols, emulsifiers, gellants, emollients, water, polymers, hydrocarbons, conditioning agents, and/or aliphatic esters.

In some embodiments, the present compositions are gluten free.

In some embodiments, the present compositions are formulated as oil-in-water emulsions, or as water-in-oil emulsions. In some embodiments, the compositions may further comprise one or more hydrocarbons, such as heptane, octane, nonane, decane, undecane, dodecane, isododecane, tridecane, tetradecane, pentadecane, hexadecane, heptadecane, octadecane, nonadecane, henicosane, docosane, and tricosane, and any saturated linear or saturated branched isomer thereof.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore, as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" is not intended to be limiting and is used in the same way that the term "comprising" is commonly used.

In the present specification, the structural formula of the compounds represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formulas describe herein. It is noted that any crystal form, crystal form mixture, or anhydride or hydrate thereof is included in the scope of the present invention.

"Tautomers" refers to compounds whose structures differ markedly in arrangement of atoms, but which exist in easy and rapid equilibrium. It is to be understood that the compounds of the invention may be depicted as different tautomers. it should also be understood that when compounds have tautomeric forms, ail tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as Na+, K+, Li+, alkali earth metal salts such as Mg2+ or Ca2+, or organic amine salts, or organic phosphonium salts.

All percentages used herein, unless otherwise indicated, are by volume.

All ratios used herein, unless otherwise indicated, are by molarity.

Although specific embodiments of the present disclosure have been described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

EXAMPLES

Having been generally described herein, the follow non-limiting examples are provided to further illustrate this invention.

The compounds disclosed herein can be prepared through a number of straightforward esterification or transesterification processes. One preferred method involves the use of combinations of $MgSO_4$ and $H_2SO_4$, in a similar vein to that of Wright, et al. in *Tetrahedron Letters*, Vol. 38, No. 42, pp. 7345-7348, 1997. In an even more preferred method, however, the $MgSO_4/H_2SO_4$ catalyst is prepared in advance from a non-polar organic solvent such as heptane.

In this approach the $MgSO_4$ is suspended in solution with stirring under inert atmosphere, (e.g., 10 g of $MgSO_4$ in 40 g of heptane), and concentrated $H_2SO_4$ is added dropwise to the solution. The mixture is stirred for some time, e.g., 15 minutes or 1 hour, and the heptane phase is then filtered off, leaving a white solid powder that can be further dried under vacuum or blown dry with inert air, e.g., nitrogen or argon. This white solid can then be used as a powerful esterification catalyst that is especially preferred for making tertiary esters from tertiary alcohols and/or suitably substituted olefins.

Example 1. Isodecyl Palmitate
(2,6-Dimethyloctan-1-yl palmitate)

2,6-Dimethyloctanol (1 equivalent) is combined with palmitic acid (1 equivalent) in hexane or heptane solvent, and 50 grams of the $MgSO_4/H_2SO_4$ solid catalyst per kilogram of 2,5-dimethyloctanal is added under an inert atmosphere in a 5-liter glass reactor vessel. The solution is then stirred for 8 hours at 80° C. with nitrogen bubbling. The gas outlet of the glass reactor is attached to a condenser to condense and collect excess methanol. The reaction is then brought to room temperature, and then 100 grams of potassium carbonate is slowly added to the solution. It is then stirred for 2 hours and filtered. Excess 2,6-dimethyloctanol and solvent is removed under reduced pressure and the desired product is further isolated by distillation.

Example 2. Isodecyl Oleate (2,4-dimethyloctan-2-yl oleate)

2,4-Dimethyloctan-2-ol (1 equivalent) is combined with oleic acid (1 equivalent) in hexane or heptane solvent, and 50 grams of the $MgSO_4/H_2SO_4$ solid catalyst per kilogram of 2,4-methyloctan-2-ol is added under an inert atmosphere in a 5-liter glass reactor vessel. The solution is then stirred for 8 hours at 100° C. with nitrogen bubbling. The gas outlet of the glass reactor is attached to a condenser to condense and collect excess water. The reaction is then brought to room temperature, and then 400 grams of potassium carbonate is slowly added to the solution. It is then stirred for 2 hours and filtered. Excess 2,4-methyloctan-2-ol and solvent is removed under reduced pressure and the desired product is further isolated by distillation.

Example 3. Isodecyl Oleate (3,7-dimethyloctan-1-yl oleate)

3,7-Dimethyl-1-octanol (a.k.a. dihydrocitronellol or tetrahydrogeraniol) (64 g, 0.40 mol) is combined with soy-derived methyl oleate (100 g, 0.34 mol). The reaction is then charged with 2.0 g of potassium methoxide and is stirred under vacuum at 55° C. in an apparatus equipped with a dry-ice cooled collection bulb. When the theoretical amount of methanol is observed to have been distilled off and collected, the reaction is brought to room temperature and ambient pressure, diluted with hexane (~200 ml), and then filtered through a pad of silica and celite to remove any inorganic material. The solvent is then removed under reduced pressure on a rotary evaporator. The resulting light yellow, translucent liquid is placed under distillation to remove any residual 3,7-dimethyl-1-octanol. 127 g (88.5% of theoretical) of light yellow, clear liquid is obtained. $^1H$ NMR ($CDCl_3$): δ: 0.85-0.92 (m, 12H); 1.10-1.18 (m, 4H); 1.20-1.36 (m, 21H); 1.38-1.45 (m, 1H); 1.48-1.56 (m, 2H); 1.58-1.68 (m, 4H); 1.96-2.06 (m, 4H), 2.25-2.31 (t, 2H); 4.05-4.14 (m, 2H); 5.30-5.37 (m, 2H).

The product of Example 3 is found to have a refractive index of 1.45100 and a surface tension of 25.9 mN/m.

Example 4. Isodecyl Palmitate (3,7-dimethyloctan-1-yl palmitate)

3,7-dimethyl-1-octanol (70 g, 0.44 mol) is combined with methyl palmitate (100 g, 0.37 mol). The reaction is then charged with 2.0 g of potassium methoxide and is stirred under vacuum at 55° C. in an apparatus equipped with a dry-ice cooled collection bulb. When the theoretical amount of methanol is observed to have been distilled off and collected, the reaction is brought to room temperature and ambient pressure, diluted with hexane (~200 ml), and then filtered through a pad of silica and celite to remove any inorganic material. The solvent is then removed under reduced pressure on a rotary evaporator. The resulting light yellow, translucent liquid is placed under distillation to remove any residual 3,7-dimethyl-1-octanol. 116 g (79.2% of theoretical) of light yellow, clear liquid is obtained. $^1H$ NMR ($CDCl_3$): δ: 0.85-0.91 (m, 12H); 1.10-1.17 (m, 2H); 1.22-1.34 (m, 28H); 1.38-1.46 (m, 1H); 1.47-1.56 (m, 2H); 1.57-1.69 (m, 3H); 2.26-2.30 (t, 2H); 4.05-4.14 (m, 2H).

The product of Example 4 is found to have a refractive index of 1.44395 and a surface tension of 25.4 mN/m.

Example 5. Isodecyl Laurate (3,7-dimethyloctan-1-yl laurate)

3,7-dimethyl-1-octanol (81 g, 0.513 mol) is combined with methyl laurate (100 g, 0.467 mol). The reaction is then charged with 2.0 g of potassium methoxide and is stirred under vacuum at 55° C. in an apparatus equipped with a dry-ice cooled collection bulb. When the theoretical amount of methanol is observed to have been distilled off and collected, the reaction is brought to room temperature and ambient pressure, diluted with hexane (~200 ml), and then filtered through a pad of silica and celite to remove any inorganic material. The solvent is then removed under reduced pressure on a rotary evaporator. The resulting clear liquid is placed under distillation to remove any residual 3,7-dimethyl-1-octanol. 132 g (83.1% of theoretical) of light yellow, clear liquid is obtained. $^1H$ NMR ($CDCl_3$): δ: 0.84-0.91 (m, 12H); 1.09-1.16 (m, 4H); 1.21-1.32 (m, 18H); 1.37-1.45 (m, 1H); 1.46-1.56 (m, 2H); 1.56-1.69 (m, 3H); 2.25-2.30 (t, 2H); 4.04-4.14 (m, 2H).

The product of Example 5 is found to have a refractive index of 1.44406 and a surface tension of 26.0 mN/m.

Example 6. Tetrahydromyrcene from Tetrahydromyrcenol (2,6-dimethyloct-2-ene as Major Isomer)

300 g of Tetrahydromyrcenol is combined with 20 g of Amberlyst H+ resin in a round bottom flask equipped with a stir bar and distillation accessories. The material is heated to 80° C. under vacuum with light nitrogen bubbling. Over ~6 hours $H_2O$ is distilled out with traces of organic entrained in the vapor phase. Once $H_2O$ no longer appears to be present in the distillate, and the conversion is indicated as complete by GC FID, the reaction is stopped and brought to room temperature. The reaction mixture is then filtered through a pad of celite and silica to remove any residual catalyst. 181 g (69% yield) of a clear, low viscosity liquid is obtained as a mixture of olefin isomers. The major isomer shows: $^1H$ NMR ($CDCl_3$) δ: 0.87-0.93 (m, 6H); 1.11-1.24 (m, 2H); 1.31-1.43 (m, 3H); 1.63-1.65 (s, 3H); 1.71-1.73 (s, 3H); 1.91-2.10 (m, 2H); 5.11-5.18 (m, 1H).

Example 7. Tetrahydromyrcene from Tetrahydrolinalool ((Z)-3,7-dimethyloct-3-ene as Major Isomer)

400 g of Tetrahydrolinalool is combined with 40 g of Amberlyst H+ resin in a round bottom flask equipped with a stir bar and distillation accessories. The material is heated to 80° C. under vacuum with light nitrogen bubbling. Over ~5 hours, $H_2O$ is distilled out with traces of organic entrained in the vapor phase. Once $H_2O$ no longer appears to be present in the distillate, and the conversion is indicated as complete by GC FID, the reaction is stopped and brought to room temperature. The reaction mixture is then filtered through a pad of celite and silica to remove any residual catalyst. 234 g (66% yield) of a clear, low viscosity liquid is obtained as a mixture of olefin isomers. $^1H$ NMR ($CDCl_3$) δ: 0.86-0.94 (m, 9H); 0.96-1.03 (m, 1H); 1.12-1.28 (m, 2H); 1.34-1.45 (m, 1H); 1.52-1.72 (m, 3H); 1.94-2.09 (m, 3H); 5.08-5.26 (m, 1H).

Example 8. Isodecyl Laurate (2,6-dimethyloctan-1-yl laurate)

2,6-dimethyloct-2-ene (14 g, 0.1 mol) is combined with 10 g of lauric acid (0.05 mol) in a large glass vial, and the vial is then charged with 1.0 g of Amberlyst H+ catalyst. The reaction is then heated to 40° C. with stirring, melting the lauric acid and forming a single liquid phase. The reaction mixture is stirred for 3 days, until $^1$H NMR and TLC show the desired product to have formed. The reaction mixture is then diluted with hexane, filtered through a pad of celite and silica to remove all catalyst, and it is then concentrated to remove hexane and residual 2,6-dimethyloct-2-ene. The resulting product, a mixture of 2,6-dimethyloctan-1-yl laurate and 2,6-dimethyl-octan-2-yl laurate, may be used crude in subsequent chemistry or further purified, e.g., via extraction, distillation, and/or chromatography.

Example 9. Isodecyl Oleate (2,6-dimethyloctan-1-yl oleate)

2,6-dimethyloct-2-ene (10 g, 0.071 mol) is combined with 5 g of oleic acid (0.018 mol) in a large glass vial, and the vial is then charged with 1.0 g of Amberlyst H+ catalyst. The reaction is then stirred at room temperature and is stirred for 3 days, until $^1$H NMR and TLC show the desired product to have formed. The reaction mixture is then diluted with hexane, filtered through a pad of celite and silica to remove all catalyst, and is then concentrated to remove hexane and residual 2,6-dimethyloct-2-ene. The resulting product, a mixture of 2,6-dimethyloctan-1-yl oleate and 2,6-dimethyl-octan-2-yl oleate, may be used crude in subsequent chemistry or further purified, e.g., via extraction, distillation, and/or chromatography.

Example 10. Isodecyl Laurate (3,7-dimethyloctan-3-yl laurate)

3,7-dimethyloct-3-ene (14 g, 0.1 mol) is combined with 10 g of lauric acid (0.05 mol) in a large glass vial, and the vial is then charged with 1.0 g of Amberlyst H+ catalyst. The reaction is then heated to 40° C. with stirring, melting the lauric acid and forming a single liquid phase. The reaction mixture is stirred until $^1$H NMR and TLC show the desired product to have formed. The reaction mixture is then diluted with hexane, filtered through a pad of celite and silica to remove all catalyst, and is then concentrated to remove hexane and residual 3,7-dimethyloct-3-ene. The resulting product, a mixture of 3,7-dimethyloctan-3-yl laurate and 3,7-dimethyl-octan-4-yl laurate, may be used crude in subsequent chemistry or further purified, e.g., via extraction, distillation, and/or chromatography.

Example 11. Isodecyl Oleate (3,7-dimethyloctan-3-yl oleate)

3,7-dimethyloct-3-ene (10 g, 0.071 mol) is combined with 5 g of oleic acid (0.018 mol) in a large glass vial, and the vial is then charged with 1.0 g of Amberlyst H+ catalyst. The reaction is then stirred at room temperature and is stirred until $^1$H NMR and TLC show the desired product to have formed. The reaction mixture is then diluted with hexane, filtered through a pad of celite and silica to remove all catalyst, and is then concentrated to remove hexane and residual 3,7-dimethyloct-3-ene. The resulting product, a mixture of 3,7-dimethyloctan-3-yl oleate and 3,7-dimethyl-octan-4-yl oleate, may be used crude in subsequent chemistry or further purified, e.g., via extraction, distillation, and/or chromatography.

The compounds of the above Examples are believed to offer numerous improved benefits over existing compounds used for the same purpose. For example, these compounds may provide one or more of: (a) lower melting point, (b) better lubricity, (c) better spreading (e.g., better spontaneous spreading on the skin), (d) higher refractive index, (e) better hydrolytic stability, and (f) better enzymatic stability.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

I claim:

1. A composition comprising at least two compounds of a formula selected from the group consisting of:

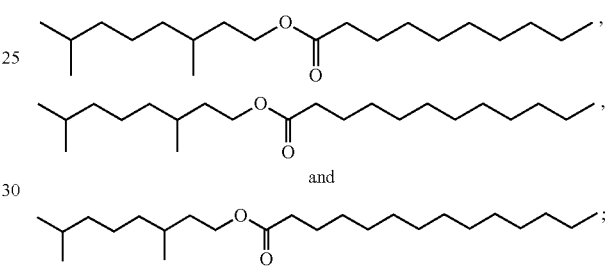

and wherein the composition is a cosmetic composition, or a personal care composition selected from a soap, skin cream or lotion, balm, shampoo, body wash, hydrating cream, deodorant, antiperspirant, after-shave lotion, cologne, perfume, or other hair care or skin care product; or a composition comprised in an air freshener, insect repellant, detergent, household cleaning product, room spray, pomander, candle, toilet water, talcum powder, shower gel, hair spray, sunscreen, or pet litter.

2. The composition according to claim 1, wherein the composition further comprises one or more pharmaceutically acceptable, cosmetically acceptable, or industrially acceptable excipients or carriers, selected from the group consisting of solvents, oils, surfactants, emollients, diluents, glidants, abrasives, humectants, polymers, plasticizer, catalyst, antioxidant, coloring agent, flavoring agent, fragrance agent, antiperspirant agent, antibacterial agent, antifungal agent, hydrocarbon, stabilizer, and viscosity controlling agent.

3. The composition of claim 1, wherein the composition is a cosmetic composition.

4. The composition of claim 1, wherein the personal care composition is selected from a soap, shampoo, body wash, deodorant, or antiperspirant.

5. A product selected from a cosmetic, soap, skin cream or lotion, balm, shampoo, body wash, hydrating cream, deodorant, antiperspirant, after-shave lotion, cologne, perfume, or other hair care or skin care product, air freshener, insect repellant, detergent, household cleaning product, room spray, pomander, candle, toilet water, talcum powder, shower gel, hair spray, sunscreen, or pet litter, comprising at least two compounds of a formula selected from the group consisting of:

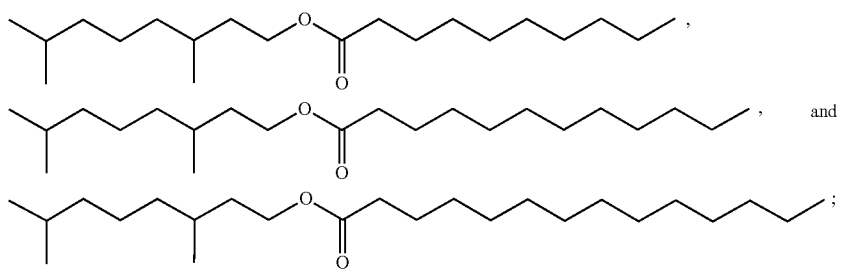

in admixture with one or more pharmaceutically acceptable, cosmetically acceptable, or industrially acceptable excipients or carriers, selected from the group consisting of solvents, oils, surfactants, emollients, diluents, glidants, abrasives, humectants, polymers, plasticizer, catalyst, antioxidant, coloring agent, flavoring agent, fragrance agent, antiperspirant agent, antibacterial agent, antifungal agent, hydrocarbon, stabilizer, and viscosity controlling agent.

6. The product of claim 5, wherein the product is a cosmetic composition.

7. The product of claim 5, wherein the product is selected from a soap, shampoo, body wash, deodorant, or antiperspirant.

8. The product of claim 6, wherein the product is selected from the group consisting of nail polish, eye liner, mascara, lipstick, foundation, concealer, blush, bronzer, eye shadow, lip liner, lip balm, and dermocosmetic.

9. The composition of claim 1, wherein the composition is a cologne or perfume.

10. The composition of claim 1, wherein the composition is an air freshener or room spray.

11. The composition of claim 1, wherein the composition comprises the compounds

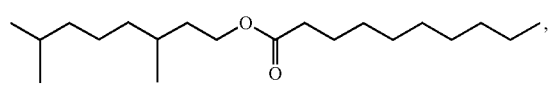 [SMILES: CCCCCCCCCC(=O)OCCC(C)CCCC(C)C]

and

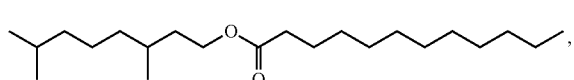

or the compounds

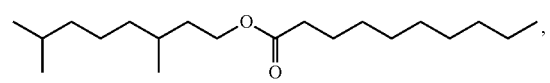 [SMILES: CCCCCCCCCC(=O)OCCC(C)CCCC(C)C]

and

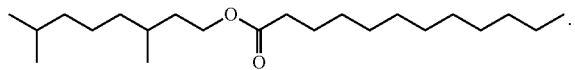 [SMILES: CCCCCCCCCCCC(=O)OCCC(C)CCCC(C)C]

12. The composition of claim 1, wherein the composition comprises the compound

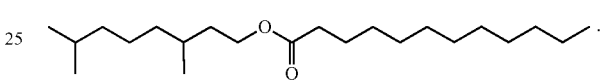

13. The composition of claim 1, wherein the composition comprises the compound

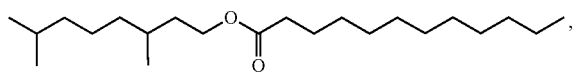 [SMILES: CCCCCCCCCCCC(=O)OCCC(C)CCCC(C)C]

and the compound

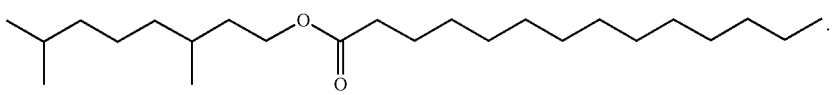 [SMILES: CCCCCCCCCCCCCC(=O)OCCC(C)CCCC(C)C]

14. The product of claim 5, wherein the product comprises the compounds

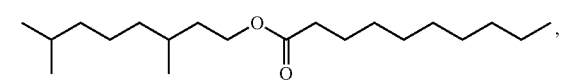 [SMILES: CCCCCCCCCC(=O)OCCC(C)CCCC(C)C]

and

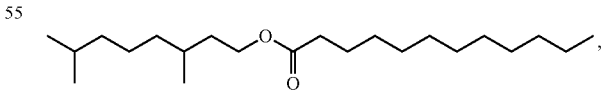

or the compounds

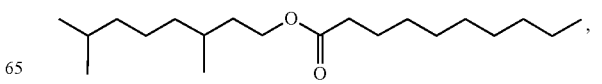

and
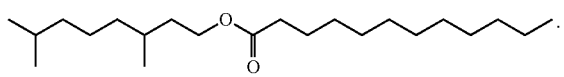 [SMILES: CCCCCCCCCCCC(=O)OCCC(C)CCCC(C)C]
15. The product of claim 5, wherein the product comprises the compound
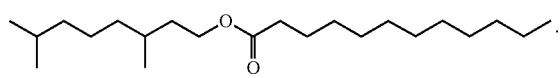 [SMILES: CCCCCCCCCCCC(=O)OCCC(C)CCCC(C)C]
16. The product of claim 5, wherein the product comprises the compound
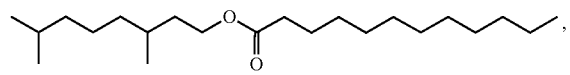 [SMILES: CCCCCCCCCCCC(=O)OCCC(C)CCCC(C)C]
and the compound
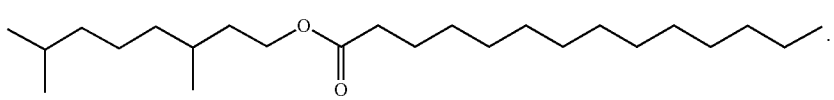 [SMILES: CCCCCCCCCCCCCC(=O)OCCC(C)CCCC(C)C]
17. The composition of claim 1, wherein the composition does not comprise the compound
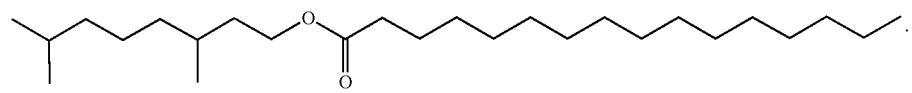 [SMILES: CCCCCCCCCCCCCCCC(=O)OCCC(C)CCCC(C)C]
18. The product of claim 5, wherein the product does not comprise the compound
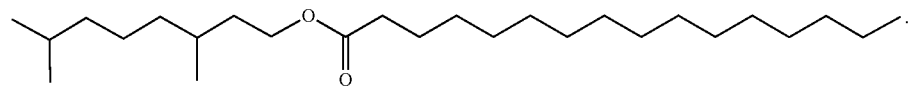 [SMILES: CCCCCCCCCCCCCCCC(=O)OCCC(C)CCCC(C)C]
* * * * *